(12) United States Patent
Ning et al.

(10) Patent No.: US 11,439,588 B2
(45) Date of Patent: Sep. 13, 2022

(54) VAGINAL SUSTAINED-RELEASE DRUG DELIVERY SYSTEM FOR LUTEAL SUPPORT, METHOD FOR PREPARATION AND USE THEREOF

(71) Applicant: National Research Institute for Family Planning, Beijing (CN)

(72) Inventors: Meiying Ning, Beijing (CN); Liangyu Xia, Beijing (CN); Xu Ma, Beijing (CN); Bin He, Beijing (CN)

(73) Assignee: NATIONAL RESEARCH INSTITUTE FOR FAMILY PLANNING, Beijing (CN)

( * ) Notice: Subject to any disclaimer, the term of this patent is extended or adjusted under 35 U.S.C. 154(b) by 0 days.

(21) Appl. No.: 16/973,737

(22) PCT Filed: Oct. 12, 2019

(86) PCT No.: PCT/CN2019/110810
§ 371 (c)(1),
(2) Date: Dec. 9, 2020

(87) PCT Pub. No.: WO2021/068239
PCT Pub. Date: Apr. 15, 2021

(65) Prior Publication Data
US 2021/0369605 A1    Dec. 2, 2021

(51) Int. Cl.
*A61K 9/00* (2006.01)
*A61K 31/57* (2006.01)
*A61K 47/32* (2006.01)

(52) U.S. Cl.
CPC ............ *A61K 9/0036* (2013.01); *A61K 31/57* (2013.01); *A61K 47/32* (2013.01)

(58) Field of Classification Search
None
See application file for complete search history.

(56) References Cited

U.S. PATENT DOCUMENTS 5,869,081 A    2/1999    Jackanicz et al.
5,989,581 A    11/1999    Groenewegen
(Continued)

FOREIGN PATENT DOCUMENTS

| | | | |
|---|---|---|---|
| CN | 102098991 A | 6/2011 | |
| CN | 104146948 A | 11/2014 | |
| CN | 109248140 A | 1/2019 | |
| WO | WO-2005089723 A1 * | 9/2005 | ........... A61K 9/0036 |

OTHER PUBLICATIONS

Progesterone (You and Your Hormones from the Society for Endocrinology, available online Jul. 8, 2017). (Year: 2017).*
(Continued)

*Primary Examiner* — Melissa S Mercier
(74) *Attorney, Agent, or Firm* — Loza & Loza, LLP; Michael F. Fedrick

(57) ABSTRACT

The present invention relates to a vaginal sustained-release drug delivery system for luteal support and a method for preparation and use thereof. The vaginal sustained-release drug delivery system for luteal support is a progesterone depot-type vaginal ring having a bilayer structure of a core layer and a film layer enclosing the core layer, wherein the core layer is composed of a solid scaffold carrier of medical EVA containing a drug uniformly dispersed therein, and the film layer is composed of a medical EVA material containing no drug. The vaginal sustained-release drug delivery system for luteal support according to the present invention can be used for assisted reproduction and for treatment of functional uterine bleeding, premenstrual syndrome and the like due to luteal phase defect with a significantly improved therapeutic effect.

11 Claims, 2 Drawing Sheets

(56) References Cited

U.S. PATENT DOCUMENTS

| | | | |
|---|---|---|---|
| 8,580,293 B2 | 11/2013 | Ahmed et al. | |
| 8,828,981 B2 | 9/2014 | Creasy et al. | |
| 2009/0202612 A1* | 8/2009 | Ahmed | A61P 5/06 424/432 |
| 2012/0202742 A1 | 8/2012 | Ron et al. | |

OTHER PUBLICATIONS

Laurel et al. (Progesterone Vaginal Ring for Luteal Support, The Journal of Obstetrics and Gynecology of India, (Jan.-Feb. 2015) 65(1):5-10). (Year: 2015).*

Helbling, Ignacio M. et al., "The Optimization of an Intravaginal Ring Releasing Progesterone Using a Mathematical Model", Pharm Res, 2014, 31:795-808.

International Search Report for International Application No. PCT/CN2019/110810 dated Dec. 10, 2019, 7 pages.

Weiss, Herman et al., "Pharmacokinetics and tolerability of a novel progesterone intravaginal ring in sheep", Drug Delivery and Translational Research, 2019, https://doi.org/10.1007/s13346-019-00646-x, 9 pages.

The Third Office Action and search report dated Jun. 1, 2022 for counterpart Chinese Patent Application No. 201980080003.1.

Zhang Maoqing et al., Xian Dai Yaolixue Yu Yaowu Zhiliao Jichu, Jilin Science and Technology Press, p. 194 (2019).

Hu Chongmao, Production and Application of Film Coating Premix for Pharmaceutical Excipients, China Medical Science and Technology Press, p. 448 (2014).

* cited by examiner

VAGINAL SUSTAINED-RELEASE DRUG DELIVERY SYSTEM FOR LUTEAL SUPPORT, METHOD FOR PREPARATION AND USE THEREOF

CROSS-REFERENCE TO RELATED APPLICATIONS

This application is the U.S. national stage of International Patent Application No. PCT/CN2019/110810, filed on Oct. 12, 2019 and entitled VAGINAL SUSTAINED-RELEASE DRUG DELIVERY SYSTEM FOR LUTEAL SUPPORT, METHOD FOR PREPARATION AND USE THEREOF, the disclosure of which is incorporated herein by reference in its entirety.

TECHNICAL FIELD

Embodiments of the present invention relate to an assisted reproductive technology, in particular, to a vaginal sustained-release drug delivery system for luteal support, a method for preparing the same, and use thereof, belonging to the technical field of pharmaceutics.

BACKGROUND ART

With nearly 40 years of rapid development of human assisted reproductive technologies, techniques including artificial insemination, in vitro fertilization and embryo transfer (IVF-ET), single sperm-oocyte microscopic intracytoplasmic sperm injection (ICSI), oocytes in vitro maturation (IVM) and the like have been developed, and luteal support has become a routine step of most assisted reproductive technologies. Current medicaments for luteal support mainly include human chorionic gonadotropin (hCG), natural progesterone, and synthetic progesterone derivatives. Among them, progesterone, as a hormone naturally secreted by the human body, has greater safety and is currently the preferred choice of medicament for luteal support.

At present, there are various types of progesterone preparations for luteal support produced domestically and internationally, mainly including oral formulations, gels, injections, and vaginal suppositories. Oral formulations of progesterone are convenient to use, but have a low blood drug level after administration, result in a low pregnancy rate due to the hepatic first pass effect, may cause systemic adverse reactions when administered at a large dose, and is rarely used alone for luteal support in assisted reproductive technologies. Progesterone injections are the most common dosage form. Though it has definite efficacy and avoids the hepatic first pass effect caused by oral administration, it tends to cause a local or even systemic allergic reaction in patients due to the irritation by an oil solution, requires daily injection which leads to poor patient compliance, and may cause skin inflammation and scab formation if injected for a long term. Vaginal preparations of progesterone such as capsules, suppositories and gels bypass the hepatic first pass effect because the uterine first-pass effect has a "targeting characteristic" and have higher bioavailability as compared to oral formulations, and are more convenient and avoid pain in patients caused by injection as compared to intramuscularly injected progesterone. Crinone (Crinone 8%), a vaginal gel approved by FDA, shows clinical efficacy the same as or better than that of intramuscularly injected progesterone, but needs one or more administrations a day and produces a considerable amount of vaginal excretion that stains clothing, which causes discomfort and dissatisfaction in patients, and may also not deliver the full dose in each administration due to drug leakage.

A progesterone vaginal ring is equivalent to a vaginal gel in terms of safety and effectiveness, but is advantageous in that it is administered at a lower frequency, is more comfortable and convenient, and allows self-depositing and removing. A vaginal ring employing a silicone rubber elastomer as the carrier material has been used in the field of contraception for many years thanks to its good biocompatibility and biological tolerance. However, silicone rubber elastomers require curing and post-curing at a high temperature and are manufactured in a complex process with a high cost. They are not reprocessible materials, cannot be recycled, and contaminate the environment because of their non-degradability. For example, CN102098991A, CN104146948A, and U.S. Pat. No. 8,580,293B2 disclose an integrated progesterone-containing vaginal ring using the MED-4840 silicone rubber elastomer as the matrix, which is manufactured in a complex process with a high cost, and is non-degradable. Furthermore, this integrated vaginal ring contains hydrocarbons or fatty acid glycerides which gradually penetrate into the user's vagina during use, causing increased vaginal excretion or staining clothing, and these substances would also be absorbed into the human body through vaginal mucosal epithelial cells, which may pose a potential threat to the health in long-term use and demands an improvement in its safety. Furthermore, this integrated vaginal ring also shows an obvious initial burst release, and tends to cause adverse reactions as the drug release amount exceeds a threshold. US005869081A discloses a progesterone vaginal ring for treatment of infertility, which uses a common silicone rubber elastomer as the carrier material and has the typical disadvantages of silicone rubber. As can be seen from its drug release curve disclosed, this drug release device releases the drug in an amount that varies greatly from day to day and cannot release the drug constantly and slowly. In addition, it has a rather long use cycle, which not only reduces the flexibility of administration but may also induce increased vaginal excretion or vaginal infection due to the long-term placement.

"The Optimization of an Intravaginal Ring Releasing Progesterone Using a Mathematical Model[J]" (Helbling I M, Ibarra J C D, Luna J A. Pharmaceutical Research, 2014, 31(3):795-808) discloses a progesterone vaginal ring for contraception during lactation, which uses ethylene-ethyl acetate copolymer (EVA) as the matrix and is prepared by a hot-melt extrusion method. In this technique, a harmful carcinogen, dichloromethane, is used to dissolve progesterone, and the manufacture of progesterone-containing EVA particles requires a complicated process and lengthy steps, is very time-consuming (this step alone needs as long as 4 hours), and may result in drug loss accompanied by solvent volatilization. In addition, this preparation is a matrix-based vaginal ring and shows an obvious initial burst release that easily causes adverse reactions.

There is a need in the prior art for improved vaginal sustained-release drug delivery systems for luteal support.

SUMMARY OF INVENTION

An object of the present invention is to provide an improved vaginal sustained-release drug delivery system for luteal support.

Another object of the present invention is to provide a method for preparing the vaginal sustained-release drug delivery system for luteal support.

Another object of the present invention is to provide related use of the vaginal sustained-release drug delivery system for luteal support.

In order to achieve the above objects, in one aspect, the present invention provides a vaginal sustained-release drug delivery system for luteal support, which is a progesterone depot-type (also referred to as the shell type or membrane controlled type) vaginal ring comprising a bilayer structure of a core layer (also referred to as drug core or matrix layer) and a film layer (also referred to as coating layer or outer layer) enclosing the core layer, wherein the core layer is composed of a solid scaffold carrier of medical EVA containing a uniformly dispersed (or dissolved) drug, and the film layer is composed of a medical EVA material without a drug.

In the present invention, a membrane-controlled vaginal ring manufactured with EVA as the carrier material has the general advantages of EVA, such as less initial drug load, less residual hormone, no additional curing or cross-linking step, less manufacturing time and cost, a better cost-benefit ratio, less environmental hazards, reprocessibility after use, and glossy and transparent appearance. Importantly, it can avoid burst release and achieve a constant and slow drug release, thereby significantly improving patient compliance.

In the vaginal sustained-release drug delivery system for luteal support according to the present invention, the core layer is made of a medical EVA material as the scaffold in which the drug is uniformly dispersed (or dissolved), has suitable elasticity and hardness, and shows high compatibility, solubility and permeability with respect to the drug. The material for the film layer is also EVA, and the EVA film layer enclosing the drug core may have a "retarding" effect against massive drug release from the drug core layer, so that the burst release effect is avoided and the drug is released more constantly and slowly. The optimal combination of two EVA materials provides better hardness and elasticity for the vaginal ring, and greatly improves patient compliance. Herein the "suitable elasticity and hardness" means the ability of a solid or semi-solid to bend or resist stress and tension without being damaged or broken, such that it does not fall off during use after being placed in the human body. For example, the depot-type vaginal ring according to the present invention can deform or bent, upon for example finger pressing, and restore its original shape when the pressure is removed. The suitable elasticity and hardness characteristics of the present invention are useful for improving patient comfort and facilitating the administration and removal of the device.

According to a specific embodiment of the present invention, in the vaginal sustained-release drug delivery system for luteal support according to the present invention, the drug in the core layer is micronized progesterone with a particle size less than 20 μm. Compared with common progesterone, micronized progesterone has an increased specific surface area, increased solubility, and a higher dissolution rate, which are beneficial to the absorption of progesterone in the vaginal mucous membrane and improve the bioavailability. Also, micronization of progesterone allows easier and more uniform dispersion of the drug in the carrier material. The "micronization" used herein means that the particles of the composition have been reduced to a micron-scale size.

According to a specific embodiment of the present invention, in the vaginal sustained-release drug delivery system for luteal support according to the present invention, the ratio of drug to EVA carrier material in the core layer ranges from 20% to 40% (w/w).

In some specific embodiments of the present invention, the vaginal sustained-release drug delivery system for luteal support according to the present invention is a closed ring-shaped article. The present invention is used to administer or apply active drugs into the vaginal and/or urogenital tract of a subject, including the vagina, cervix or uterus of a female. Here the "ring-shaped article" refers to a shape of a ring, a shape related to a ring, or formation of a ring. A ring shape suitable for the present invention includes a loop, an oval shape, an ellipse shape, a circular ring shape, and the like.

In some specific embodiments of the present invention, the progesterone is uniformly dispersed in the EVA carrier material.

In the present invention, EVA is polyethylene-vinyl acetate copolymer, and the model name of EVA is designated according to the content of VA (vinyl acetate). For example, EVA33 means a VA content of 33% (33 wt % VA). In some specific embodiments of the present invention, the EVA in the core layer has a VA content of 10-40 wt %. In some specific embodiments of the present invention, the EVA in the film layer has a VA content of 18-40 wt %. In addition, the EVA materials used in the core layer and the film layer may be the same or different. They are chosen to be the same or different to serve the purpose of making the drug release constant, in order to avoid adverse reactions as much as possible.

The vaginal sustained-release drug delivery system for luteal support according to the present invention, as a depot-type vaginal ring, can have any dimension suitable for placement in the vagina. In some specific embodiments of the present invention, the outer diameter of the ring is about 50-60 mm, wherein the "outer diameter" refers to the length of any line segment that passes through the center of the ring and ends on the outer circumference of the ring; the inner diameter of the ring is about 38-52 mm, wherein the "inner diameter" refers to the length of any line segment that passes through the center of the ring and ends on the inner circumference of the ring; and the cross-sectional diameter is about 4-6 mm, wherein the "cross-sectional diameter" refers to the length of any line segment that ends on the inner and outer circumferences of the ring, including the thickness of the release-controlling film.

In some specific embodiments of the present invention, in the vaginal sustained-release drug delivery system for luteal support according to the present invention, the film layer has a thickness of 0.05-0.5 mm.

The method for preparation and the constitution of the vaginal sustained-release drug delivery system for luteal support according to the present invention may be adjusted and modified according to practical applications in order to achieve a constant and slow release within the threshold of an effective dose, which allows the present invention to have a better luteal supporting effect and a better reproductive assisting effect, and also fully takes into account the individual difference among users. The adjustments and modifications mainly include: A) adjustments and modifications in the material, structural specification and constitution of the drug core scaffold of the aforementioned depot-type vaginal ring according to practical needs, involving: 1) choosing different EVA scaffold materials (also referred to as drug carrier materials or drug matrix materials); 2) choosing a progesterone-to-EVA ratio that meets requirements; and 3) choosing drug core scaffolds with different ring diameters or cross-sectional diameters; and B) adjustments and modifications in the materials and constitution of the aforementioned release-controlling film according to practical needs, involving: 1) choosing different materials for the release-controlling film (or EVA film materials); and 2) choosing different thicknesses for the release-controlling film.

In some specific embodiments of the present invention, for the vaginal sustained-release drug delivery system for luteal support according to the present invention, the in vivo release rate of the drug (such as micronized progesterone) is controlled at about 10 mg/d to about 20 mg/d. In some more specific embodiments, the drug is released from the vaginal ring in vivo at about 10 mg/d to about 15 mg/d.

In some specific embodiments of the present invention, for the vaginal sustained-release drug delivery system for luteal support according to the present invention, the drug is controlled to be released at a stable rate over a period of about 1 day to about 14 days. In some more specific embodiments, progesterone is released at a stable rate for about 1 day to about 7 days or for about 7-14 days.

In another aspect, the present invention also provides a method for preparing the vaginal sustained-release drug delivery system for luteal support, comprising:

mixing the drug and powder of an EVA matrix thoroughly and uniformly, heating the mixture to melt in a screw extruder, and extruding and molding the melt into a bar-shaped drug core; winding the extruded bar-shaped drug core around a winding and unwinding device;

co-extruding and molding the bar-shaped drug core and an EVA film material in a screw extruder equipped with a 2-layer concentric annular co-extrusion die, with the extruded release-controlling film being in the outer layer and the bar-shaped drug core passing within the inner layer of the 2-layer concentric annular co-extrusion die, to form a bar-shaped drug rod with a release-controlling film layer enclosing the drug core after the drug core and the release-controlling film leave the die exit of the co-extrusion die;

cutting the drug rod to a predetermined length, and joining both ends thereof together to form a ring-shaped vaginal sustained-release drug delivery system.

According to a specific embodiment of the present invention, in the method for preparation according to the present invention, the powder of an EVA matrix can be obtained by pre-pulverization of commercially available EVA particles, in particular, by pulverizing and grinding at an ultra-low temperature, cooling to −196° C. with liquid nitrogen, and pulverizing into fine powder in a size of 100 mesh in a cryogenic pulverizer.

In some specific embodiments of the present invention, after an appropriate amount of drug and the pulverized powder of the EVA matrix are mixed thoroughly and uniformly, the mixture is placed in a twin-screw extruder and heated and molten, and a bar-like cylindrical drug core is extruded through the die exit. The drug core meets various requirements on thickness (the cross-sectional diameter) by adjustment of the rotation speed gear of the conveyer belt provided in the extruder. According to specific embodiments of the present invention, during extrusion of the drug core, the temperature of the extruder may be controlled at: 60 to 110° C. in the first zone, 65 to 120° C. in the second zone, and 60 to 120° C. in the third zone.

In some specific embodiments of the present invention, the extruded bar-like drug core can be neatly wound on a winding and unwinding device, ready for later use.

In some specific embodiments of the present invention, an EVA film material is added to the screw extruder. The exit of the extruder is connected to a 2-layer concentric annular co-extrusion die, through which the extruded release-controlling film is in the outer layer, and the drug core passes within the inner layer of the 2-layer concentric annular co-extrusion die (specifically, the temperature of the extruder can be set as: 45 to 80° C. in the first zone, 65 to 100° C. in the second zone, 85 to 120° C. in the third zone, and 95 to 140° C. in the fourth zone). The winding and unwinding device and the screw extruder are started. While the winding and unwinding device draws the drug core, the release-controlling film is extruded by the screw extruder through the 2-layer concentric annular co-extrusion die (the extrusion rate can be controlled at 10-20 rpm), such that both the drug core and the release-controlling film pass through the die exit of the co-extrusion die to form a 2-layer concentric rod with a release-controlling film (drug rod). The rod is cooled down in a water trough and drawn by the winding and unwinding device such that it has a uniform rod thickness and no interface between layers (specifically, the rotation rate for winding and unwinding device may be controlled at 800 to 1300 rpm).

In some specific embodiments of the present invention, the drug rod is cut to a predetermined length, and both ends thereof are joined together by means of butt welding, secondary molding, solvent welding and the like to form the final depot-type ring.

In another aspect, the present invention also provides use of the vaginal sustained-release drug delivery system for luteal support in assisted reproduction. The present invention may be used as a part of assisted reproductive technology (ART) treatment of infertile women with progesterone deficiency, and can also be used for luteal phase supplementation or replacement, e.g., partial luteal support for in vitro fertilization or complete luteal support for oocyte transplantation.

In another aspect, the present invention also provides use of the vaginal sustained-release drug delivery system for luteal support in the manufacture of a drug delivery system for treatment of functional uterine bleeding and/or premenstrual syndrome due to luteal phase defect.

Furthermore, the present invention also provides a method for applying the vaginal sustained-release drug delivery system in assisted reproductive treatment, and also provides a method for applying the vaginal sustained-release drug delivery system in treatment of functional uterine bleeding and/or premenstrual syndrome due to luteal phase defect.

In some specific embodiments of the present invention, in practical application of the vaginal sustained-release drug delivery system for luteal support according to the present invention, progesterone is released in vivo from the vaginal ring at about 10 mg/d to about 20 mg/d. In some further specific embodiments, progesterone is released in vivo from the vaginal ring at about 10 mg/d to about 15 mg/d.

In some specific embodiments of the present invention, in practical application of the vaginal sustained-release drug delivery system for luteal support according to the present invention, progesterone is released at a stable rate for about 1 to about 14 days. In some further specific embodiments, progesterone is released at a stable rate for about 1 to about 7 days. The vaginal sustained-release drug delivery system for luteal support according to the present invention can be replaced regularly depending on the drug release duration, e.g., replaced about 7 days after administered to a patient.

Advantageous Effect of the Invention

The present invention provides an EVA depot-type vaginal ring and a method for preparation thereof, useful for assisted reproduction as well as for functional uterine bleeding, premenstrual syndrome and the like caused by luteal phase defect, to address the issues of progesterone preparations for assisted reproduction in the prior art, such as inadequate efficacy, inconstant drug release, poor compliance, a high manufacturing cost, a low cost-effectiveness ratio in large-scale production, and poor safety. The vaginal sustained-release drug delivery system for luteal support according to the present invention has a significantly improved therapeutic effect as compared to common matrix-type vaginal rings.

DETAILED DESCRIPTION OF INVENTION

To provide a better understanding of the technical features, objectives and beneficial effects of the present invention, the technical solutions of the present invention will be described in details below in connection with specific examples. It should be understood that these examples are only to illustrate the present invention and not to limit the scope of the present invention. In each example, the experimental methods without specifying the conditions are conventional methods with conventional conditions well known in the art, or operated according to the conditions recommended by the manufacturer of instrument.

Example 1

Figure 1:
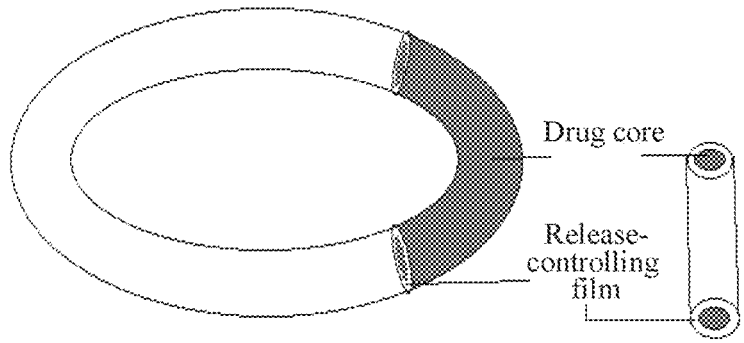
FIG. 1 is a schematic representation of the structure of the depot-type vaginal ring according to the present invention.
Figure 2:
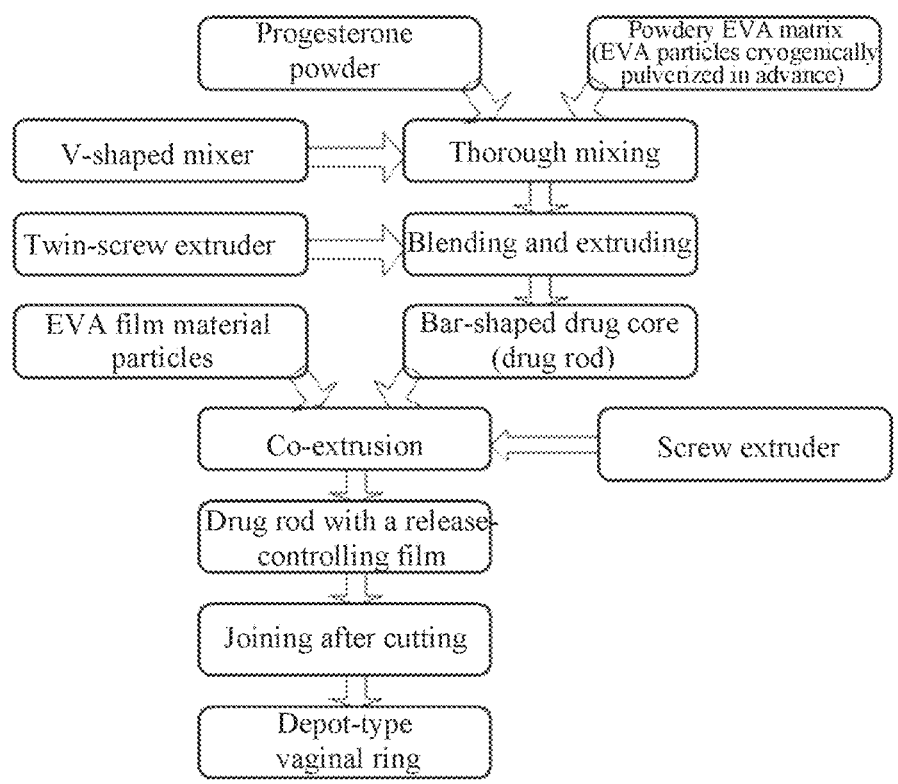
FIG. 2 is a process flow chart of the depot-type vaginal ring according to the present invention.

FIG. 1 shows the structure of the depot-type vaginal ring according to the present invention. FIG. 2 shows a process flow chart of the method for preparing the vaginal sustained-release drug delivery system for luteal support according to the present invention.

45 g of micronized progesterone and 150 g of powdery EVA33 (VA content 33%) matrix were mixed and stirred thoroughly for 5 minutes, and the mixture was then transferred to a conical twin-screw extruder in which the temperature was set at: 70° C. in the first zone, 80° C. in the second zone, and 75° C. in the third zone. The mixture was heated, melted, and extruded into a bar-like cylindrical drug core, while the conveyer speed was adjusted to control the thickness of the drug core between 4.0-4.4 mm, and the drug core was briefly cooled before neatly wound on a winding and unwinding device. Subsequently, approximately 20 g of an EVA33 (VA content 33%) film material was weighed and added into another screw extruder, and the winding and unwinding device and the screw extruder (extrusion rate 10-20 rpm) were simultaneously started. The temperature of the extruder was set at: 60° C. in the first zone, 80° C. in the second zone, 100° C. in the third zone, and 120° C. in the fourth zone, and the drawing speed of the winding and unwinding device was 1100-1200 rpm. While the winding and unwinding device drew the drug core, the release-controlling film was extruded by the screw extruder through a 2-layer concentric annular co-extrusion die, such that both the drug core and the release-controlling film were co-extruded through the co-extrusion die to form a 2-layer concentric rod with the release-controlling film, which was cooled down in a water trough and drawn by the winding and unwinding device to have a uniform rod thickness and no interface between layers. The rod was then cut into 16±1 cm long segments, and both ends thereof were joined together by means of butt welding and the like to finally form a depot-type vaginal ring having a cross-sectional diameter of about 4.50 mm, a release-controlling film thickness of about 0.13 mm, and an outer diameter of the ring of about 59.21 mm.

Figure 3:
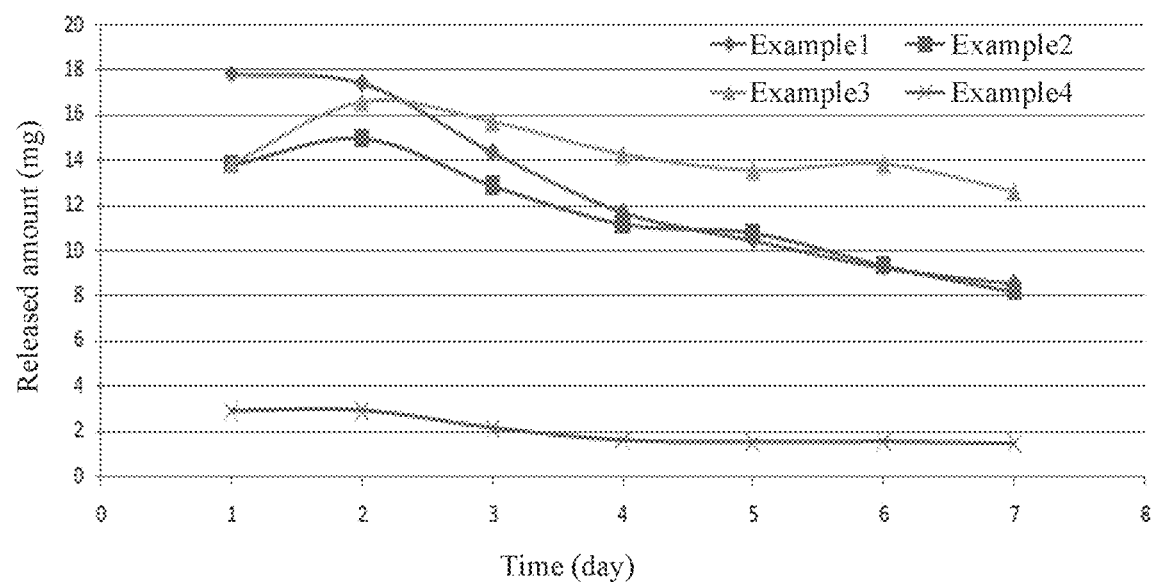
FIG. 3 is the in vitro dissolution curves of the depot-type vaginal rings of various examples of the present invention.

The in vitro dissolution curve of the depot-type vaginal ring was obtained in accordance with the Chinese Pharmacopoeia (2015 Edition, Volume IV, 0931 Method 2) under the conditions of 750 mL 0.25% SDS as the dissolution medium, 37° C.±0.5° C., and 50 r/min, and the result is shown in FIG. 3. After administered to a patient, this depot-type vaginal ring released about 10 mg to 20 mg progesterone per day for about 7 days.

Example 2

40 g of micronized progesterone and 200 g of powdery EVA16 (VA content 33%) matrix were mixed and stirred thoroughly for 5 minutes, and the mixture was then transferred to a conical twin-screw extruder in which the temperature was set at: 108° C. in the first zone, 118° C. in the second zone, and 116° C. in the third zone. The mixture was heated, melted, and extruded into a bar-like cylindrical drug core, while the conveyer speed was adjusted to control the thickness of the drug core between 3.5-4.0 mm, and the drug core was briefly cooled before neatly wound on a winding and unwinding device. Subsequently, approximately 30 g of an EVA40 (VA content 40%) film material was weighed and added into another screw extruder, and the winding and unwinding device and the screw extruder (extrusion rate 10-20 rpm) were simultaneously started. The temperature of the extruder was set at: 45° C. in the first zone, 65° C. in the second zone, 85° C. in the third zone, and 95° C. in the fourth zone, and the drawing speed of the winding and unwinding device was 800-900 rpm. While the winding and unwinding device drew the drug core, the release-controlling film was extruded by the screw extruder through a 2-layer concentric annular co-extrusion die, such that both the drug core and the release-controlling film were co-extruded through the co-extrusion die to form a 2-layer concentric rod with the release-controlling film, which was cooled down in a water trough and drawn by the winding and unwinding device to have a uniform rod thickness and no interface between layers. The rod was then cut into 16±1 cm long segments, and both ends thereof were joined together by means of butt welding and the like to finally form a depot-type vaginal ring having a cross-sectional diameter of about 4.40 mm, a release-controlling film thickness of about 0.20 mm, and an outer diameter of the ring of about 56.63 mm.

The in vitro dissolution curve of the depot-type vaginal ring was obtained in accordance with the Chinese Pharmacopoeia (2015 Edition, Volume IV, 0931 Method 2) under the conditions of 750 mL 0.25% SDS as the dissolution medium, 37° C.±0.5° C., and 50 r/min, and the result is shown in FIG. 3. After administered to a patient, this depot-type vaginal ring released about 10 mg to 20 mg progesterone per day for about 7 days.

Example 3

80 g of micronized progesterone and 200 g of powdery EVA40 (VA content 40%) matrix were mixed and stirred thoroughly for 5 minutes, and the mixture was then transferred to a conical twin-screw extruder in which the temperature was set at: 60° C. in the first zone, 70° C. in the second zone, and 65° C. in the third zone. The mixture was heated, melted, and extruded into a bar-like cylindrical drug core, while the conveyer speed was adjusted to control the thickness of the drug core between 4.4-4.7 mm, and the drug core was briefly cooled before neatly wound on a winding and unwinding device. Subsequently, approximately 40 g of an EVA18 (VA content 18%) film material was weighed and added into another screw extruder, and the winding and unwinding device and the screw extruder (extrusion rate 10-20 rpm) were simultaneously started. The temperature of the extruder was set at: 80° C. in the first zone, 100° C. in the second zone, 120° C. in the third zone, and 140° C. in the fourth zone, and the drawing speed of the winding and unwinding device was 1200-1300 rpm. While the winding and unwinding device drew the drug core, the release-controlling film was extruded by the screw extruder through a 2-layer concentric annular co-extrusion die, such that both the drug core and the release-controlling film were co-extruded through the co-extrusion die to form a 2-layer concentric rod with the release-controlling film, which was cooled down in a water trough and drawn by the winding and unwinding device to have a uniform rod thickness and no interface between layers. The rod was then cut into 16±1 cm long segments, and both ends thereof were joined together by means of butt welding and the like to finally form a depot-type vaginal ring having a cross-sectional diameter of about 5.86 mm, a release-controlling film thickness of about 0.10 mm, and an outer diameter of the ring of about 59.95 mm.

The in vitro dissolution curve of the depot-type vaginal ring was obtained in accordance with the Chinese Pharmacopoeia (2015 Edition, Volume IV, 0931 Method 2) under the conditions of 750 mL 0.25% SDS as the dissolution medium, 37° C.±0.5° C., and 50 r/min, and the result is shown in FIG. 3. After administered to a patient, this depot-type vaginal ring released about 10 mg to 20 mg progesterone per day for about 7 days.

Example 4

45 g of micronized progesterone and 150 g of powdery EVA28 (VA content 28%) matrix were mixed and stirred thoroughly for 5 minutes, and the mixture was then transferred to a conical twin-screw extruder in which the temperature was set at: 105° C. in the first zone, 110° C. in the second zone, and 105° C. in the third zone. The mixture was heated, melted, and extruded into a bar-like cylindrical drug core, while the conveyer speed was adjusted to control the thickness of the drug core between 4.0-4.4 mm, and the drug core was briefly cooled before neatly wound on a winding and unwinding device. Subsequently, approximately 30 g of an EVA9 (VA content 33%) film material was weighed and added into another screw extruder, and the winding and unwinding device and the screw extruder (extrusion rate 10-20 rpm) were simultaneously started. The temperature of the extruder was set at: 80° C. in the first zone, 100° C. in the second zone, 120° C. in the third zone, and 140° C. in the fourth zone, and the drawing speed of the winding and unwinding device was 900-1100 rpm. While the winding and unwinding device drew the drug core, the release-controlling film was extruded by the screw extruder through a 2-layer concentric annular co-extrusion die, such that both the drug core and the release-controlling film were co-extruded through the co-extrusion die to form a 2-layer concentric rod with the release-controlling film, which was cooled down in a water trough and drawn by the winding and unwinding device to have a uniform rod thickness and no interface between layers. The rod was then cut into 16±1 cm long segments, and both ends thereof were joined together by means of butt welding and the like to finally form a depot-type vaginal ring having a cross-sectional diameter of about 4.00 mm, a release-controlling film thickness of about 0.23 mm, and an outer diameter of the ring of about 57.35 mm.

The in vitro dissolution curve of the depot-type vaginal ring was obtained in accordance with the Chinese Pharmacopoeia (2015 Edition, Volume IV, 0931 Method 2) under the conditions of 750 mL 0.25% SDS as the dissolution medium, 37° C.±0.5° C., and 50 r/min, and the result is shown in FIG. 3.

Application Effects of the Products of the Examples

The progesterone depot-type vaginal rings of Examples 1 to 3 according to the present invention are convenient to use, and patients can use them by themselves without aid of medical professionals or causing an injury during administration. One ring can be used for 7-14 days, which greatly reduces the number of administrations and improves patient compliance. Also, it has a uterine targeting effect (the drug can directly act on uterus through vagina, and exerts sufficient efficacy at a very low blood drug level), and slowly and constantly releases 10-20 mg progesterone every day, avoiding the peak-to-valley effect in the blood drug level. The vaginal ring not only has high bioavailability, but also greatly reduces the toxic and side effects of the drug, improving safety in administration.

What is claimed is:

1. A vaginal sustained-release drug delivery system for luteal support comprising a progesterone depot-type vaginal ring having a bilayer structure, the bilayer structure comprising of a core layer and a film layer enclosing the core layer,
    wherein the core layer is composed of a solid scaffold carrier made of medical polyethylene vinyl acetate copolymer (EVA) material in which a drug is uniformly dispersed, wherein the drug comprises progesterone,
    wherein the film layer is composed of a medical EVA material containing no drug, and
    wherein the in vivo release rate of the drug is controlled at about 10 mg/d to about 20 mg/d.

2. The vaginal sustained-release drug delivery system for luteal support according to claim 1, wherein the drug in the core layer is micronized progesterone.

3. The vaginal sustained-release drug delivery system for luteal support according to claim 1, wherein the weight ratio of drug to EVA material in the core layer is 20:100 to 40:100.

4. The vaginal sustained-release drug delivery system for luteal support according to claim 1, which is a closed ring-shaped article.

5. The vaginal sustained-release drug delivery system for luteal support according to claim 4, wherein the ring has an outer diameter of 50 to 60 mm, an inner diameter of 38 to 52 mm, and a cross-sectional diameter of 4 to 6 mm.

6. The vaginal sustained-release drug delivery system for luteal support according to claim 4, wherein the thickness of the film layer is 0.05 to 0.5 mm.

7. The vaginal sustained-release drug delivery system for luteal support according to claim 1, wherein the drug is controlled to be released at a stable rate over a period of about 1 day to about 14 days.

8. A method of assisted reproduction, comprising administering the vaginal sustained-release drug delivery system for luteal support according to claim 1 to a subject in need thereof.

9. A method for treating functional uterine bleeding and/or premenstrual syndrome caused by luteal phase defect, comprising administering the vaginal sustained-release drug delivery system for luteal support according to claim 1 to a subject in need thereof.

10. The method according to claim 8, wherein the drug in the vaginal sustained-release drug delivery system is released at a stable rate for about 1 day to about 14 days.

11. The method according to claim 9, wherein the drug in the vaginal sustained-release drug delivery system is released at a stable rate for about 1 day to about 14 days.

* * * * *